(12) United States Patent
Daniels et al.

(10) Patent No.: US 12,383,363 B2
(45) Date of Patent: Aug. 12, 2025

(54) MENSTRUAL CUP CASE

(71) Applicant: Courtesy Cups, LLC, N. Canton, OH (US)

(72) Inventors: Savannah Daniels, Balitomore, MD (US); Douglas Paige, Lakewook, OH (US)

(73) Assignee: Courtesy Cups, LLC, North Canton, OH (US)

( * ) Notice: Subject to any disclaimer, the term of this patent is extended or adjusted under 35 U.S.C. 154(b) by 368 days.

(21) Appl. No.: 17/981,578

(22) Filed: Nov. 7, 2022

(65) Prior Publication Data

US 2023/0141755 A1 May 11, 2023

Related U.S. Application Data

(60) Provisional application No. 63/276,059, filed on Nov. 5, 2021.

(51) Int. Cl.
| | | |
|---|---|---|
| *A61B 50/31* | (2016.01) | |
| *A61B 50/00* | (2016.01) | |
| *A61F 5/00* | (2006.01) | |
| *A61F 5/455* | (2006.01) | |

(52) U.S. Cl.
CPC ............ *A61B 50/31* (2016.02); *A61F 5/4553* (2013.01); *A61B 2050/0066* (2016.02)

(58) Field of Classification Search
CPC ............. A61B 50/31; A61B 2050/0066; A61F 5/4553
See application file for complete search history.

(56) References Cited

U.S. PATENT DOCUMENTS

| | | | | |
|---|---|---|---|---|
| 1,891,761 | A * | 12/1932 | Goodard | A61F 5/4553 |
| | | | | 604/330 |
| 4,703,752 | A * | 11/1987 | Gabbay | A61F 6/08 |
| | | | | 128/841 |
| 4,848,363 | A * | 7/1989 | Cattanach | A61F 5/4553 |
| | | | | 128/834 |
| 6,168,609 | B1 * | 1/2001 | Kamen | A61F 5/4553 |
| | | | | 600/573 |
| 6,332,878 | B1 * | 12/2001 | Wray | A61F 5/4556 |
| | | | | 128/830 |
| 10,973,496 | B2 * | 4/2021 | Naseri | A61B 10/0291 |
| 2019/0099166 | A1 * | 4/2019 | Naseri | A61F 13/15 |
| 2022/0031898 | A1 * | 2/2022 | Lequay | A61L 2/26 |
| 2022/0331146 | A1 * | 10/2022 | Brush | A61F 5/4553 |

FOREIGN PATENT DOCUMENTS

| | | |
|---|---|---|
| KR | 202000021 | 10/2020 |
| WO | 2020060424 | 3/2020 |
| WO | 202213639 | 6/2022 |

OTHER PUBLICATIONS

Lucas Secades Casino, Design and Development of a Sterilizer and Cleaner Device for Menstrual Cups, Universite Libre de Bruxelles, Masters Thesis, published Aug. 16, 2020.

* cited by examiner

*Primary Examiner* — Guy K Townsend

(74) *Attorney, Agent, or Firm* — Fox Rothschild LLP

(57) ABSTRACT

The present invention generally relates to a carrying and cleaning case for a menstrual cup. In particular, the carrying and cleaning case for a menstrual cup is configured with at least two, but preferably three, segments comprising of a cleaning segment and a drying segment. The exterior of the case is configured with finger grips to prevent slippage.

20 Claims, 6 Drawing Sheets

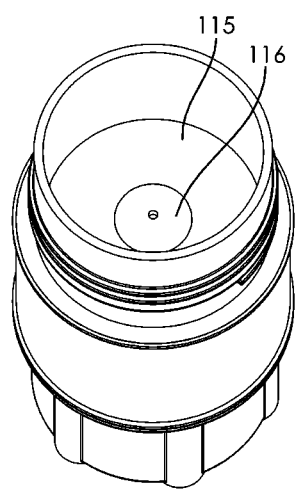
FIG. 4a
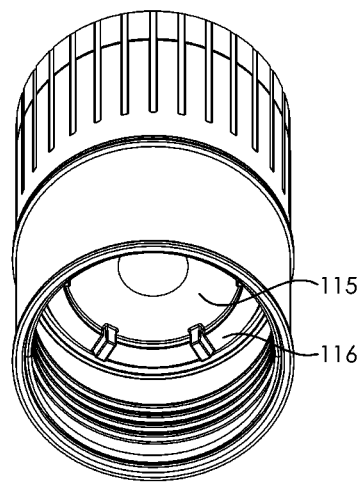
FIG. 4b
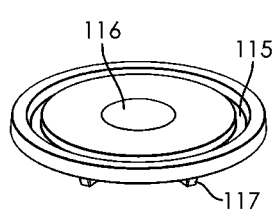
FIG. 4c
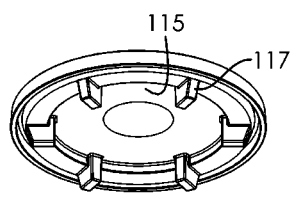
FIG. 4d
FIG. 4

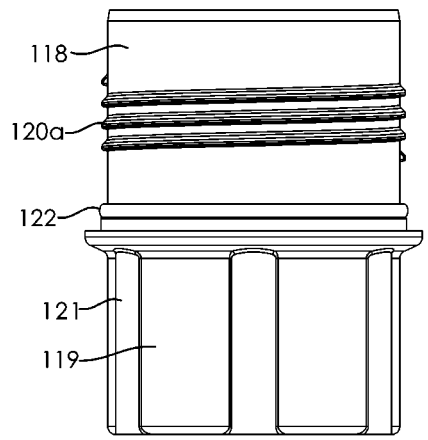
FIG. 5
FIG. 5a
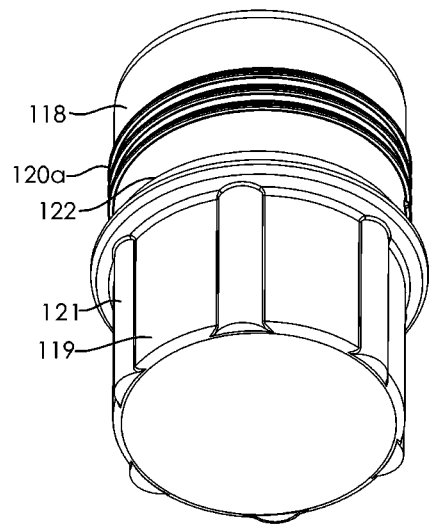
FIG. 5b
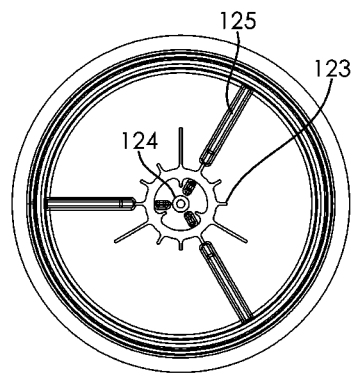
FIG. 5c

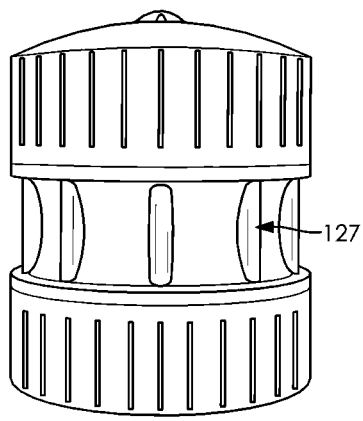
FIG. 8a
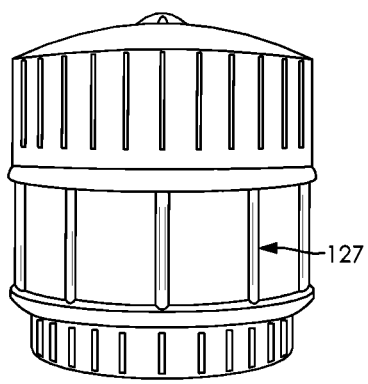
FIG. 8b
FIG. 8

MENSTRUAL CUP CASE

CROSS-REFERENCE TO RELATED APPLICATIONS

This application claims priority to U.S. provisional patent application 63/276,059 filed on Nov. 5, 2021, and entitled "Menstrual Cup Case," the entire disclosure of which is incorporated herein by reference.

FIELD OF THE INVENTION

The present invention generally relates to a cleaning device for feminine product, and more particularly to a portable cleansing case for menstrual cups.

BACKGROUND

Hygiene is a critical aspect of menstrual management as it can reduce or prevent avoidable health repercussions. And the degree of repercussions can vary from annoyance in the form of skin irritation to fatality. Menstrual blood creates a warm, moist environment that is attractive to bacteria. An imbalance in the residential bacterial flora in the vagina and surrounding area are a common cause of numerous infections.

Among the various feminine hygiene products, menstrual cups are becoming an increasingly popular option. In addition to being more sustainable—they are reusable for up to ten years—and more cost-efficient—they are expected to save at least $500 over the life of the product—they are a safer option. Women who use menstrual cups on average experience fewer infections than women using other types of feminine hygiene products. Because of these benefits, women who live and/or work in austere environments find menstrual cups to be a better option compared to some other feminine hygiene products.

However, a major drawback to menstrual cup use is the need to clean and sanitize the cup. Cleaning can be problematic when there is a lack of water and/or electricity and/or other resources that facilitate cleansing.

Existing menstrual cup cases rely on unnecessary features that, if broken or lost, render the case ineffective. As an example, WO2022136395 teaches a device for cleaning menstrual cups that includes a brushed attached to an inner ceiling. Without the brush, there is insufficient friction for proper cleaning.

The present invention is a case for menstrual cups. In particular the menstrual case allows for the storage, cleansing, and drying of menstrual cups in a portable manner. These and other features and advantages of the present invention will be explained and will become obvious to one skilled in the art through the summary of the invention that follows.

SUMMARY OF THE DISCLOSURE

The present disclosure is directed to an apparatus and associated methods related to the apparatus, namely a menstrual cup case. In an illustrative example configured for any type of menstrual cup (i.e. collapsible or non-collapsible), the menstrual cup case comprises of three components: the superior segment, the median segment, and the inferior segment. In the preferred embodiment, the three segments combine into a generally hollow, cylindrical form.

According to the preferred embodiment, the median segment serves as the connection piece for the other segments of the menstrual case. Specifically, the median segment comprises of one or more attachment means (or connection means) that reversibly affixes the superior segment and inferior segment. According to one embodiment, the median segment is configured with a top division and a bottom division that are used for integrating with the other segments. The top division reversibly attaches to the superior segment by an attachment means while the bottom division reversibly attaches to the inferior segment via another attachment means.

Within the interior of the menstrual cup case, the superior and inferior segments serve unique functions. In embodiments, the median segment is fashioned with a physical divider, preferably a gasket, which enables the median segment to provide space to the superior and inferior segments for storage and cleaning. In the preferred embodiment, the inferior segment serves as the cleansing unit for menstrual cups. Once the menstrual cup has been washed in the inferior segment, the menstrual cup is transferred to the superior segment which is configured with holes in the top surface to facilitate evaporation.

According to alternative embodiments, the invention comprises of three reversibly integrated segments that form two cavities, namely a washing cavity and a storage cavity. In greater detail, the invention comprises of a superior segment, median segment, and inferior segment. The median segment is divided into two compartments or areas. The division can be through a removable piece such as a gasket or it can be permanent piece such as a physical barrier within the median segment. Furthermore, the median segment is fashioned to integrate or connect with the other segment. According to certain embodiments, the median segment is configured with a top division and a bottom division. The top division attaches within the underside of the superior segment; meanwhile the bottom division of the median segment attaches to the inferior segment by fitting over the external surface of the inferior segment. According to some embodiments, the top division and bottom division of the median segment are structurally different so that a user does not integrate the segments in the wrong order. Once the segments are assembled together, the menstrual cup case comprises of two independent cavities.

Various embodiments may achieve one or more advantages. For example, the size of the current case may be extended and/or enlarged to encase more traditional, non-collapsible menstrual cups. As another example, the entirety of the menstrual case may be configured with a cylindrical sidewall comprising of a plurality of helical segments thereby allowing the case to be reversibly collapsible. In alternate embodiments, at least one segment comprises of the helical segment configuration such that only one segment is collapsible.

According to alternative embodiments, the menstrual cup is collapsible in a vertical fashion. The vertical collapsibility of select embodiments solve for off-gassing without the need for an additional ventilation system. Briefly, each segment is comprised of flexible material such as silicone. When vertically collapsing, pressure is applied to the superior segment, which deflates into a more planer orientation. With continued pressure, the median segment and the inferior segment also flatten.

As another example, additional weight, may be configured within the inferior segment to provide stability and prevent spillage. The additional weight may be added in various forms including using heavier material to construct the inferior segment or adding weighted components (e.g. adding a cap comprised of weighted material).

Depending on the type of cleaner used, excessive gas pressure can increase due to the mixing of reagents. In particular, when using a platinum disk, the combination of hydrogen peroxide within the disk and water can release oxygen within the menstrual cup. Accordingly, alternative embodiments of the current invention include a ventilation or venting system. Such a system requires a precise hole or silt in one or more of the segments through which excess pressure can be released in a controlled manner. In even further alternative embodiments, the menstrual cup case may be configured with a reverse flow valve.

To cleanse using the menstrual cup case, a cleaning agent may be added. Alternatively, the case may be configured with a cleaning agent or a reagent that reacts with a readily available solvent such as water.

The details of various embodiments are set forth in the accompanying drawings and the description below. Other features and advantages will be apparent from the description and drawings, and from the claims.

BRIEF DESCRIPTION OF THE DRAWINGS

Embodiments of the present invention will now be described, by way of example, with reference to the following diagram wherein:

FIG. 4 illustrates multiple views of a gasket as incorporated in the preferred embodiment of the current invention. FIG. 4(a) and FIG. 4(b) illustrate the top and bottom perspective views of the gasket within a median segment. FIG. 4(c) and FIG. 4(d) illustrate the top and bottom isolated views of the gasket.

FIG. 5 illustrates multiple views of the inferior segment. FIG. 5(a) illustrates a front-facing view whereas FIG. 5(b) illustrates a bottom-facing view of the inferior segment. FIG. 5(c) illustrates an interior view of the inferior segment.

FIG. 8 illustrates various embodiments of the current invention. FIG. 8(a) illustrates a first alternative embodiment. FIG. 8(b) presents a second alternative embodiment.

DETAILED DESCRIPTION OF EMBODIMENTS

Figure 1:
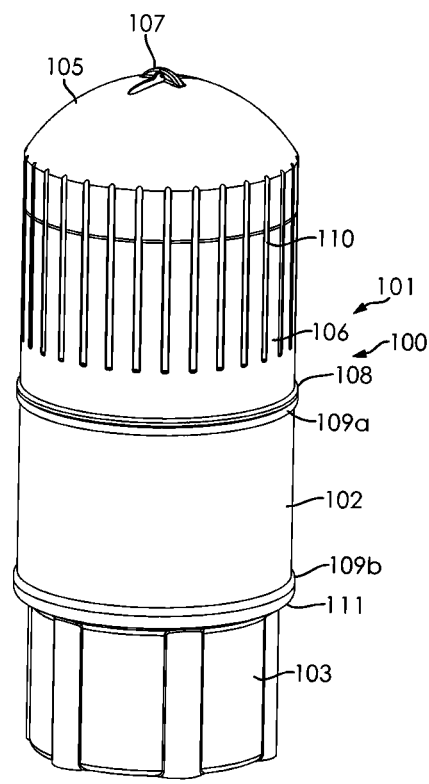
FIG. 1 illustrates a front-facing view of the preferred embodiment of the current invention.

In the Summary above and in this Detailed Description, and the Listing of Claims below, and in the accompanying drawings, reference is made to particular features of various embodiments of the invention. It is to be understood that the disclosure of embodiments of the invention in this specification includes all possible combinations of such particular features. For example, where a particular feature is disclosed in the context of a particular aspect or embodiment of the invention, or a particular claim, that feature can also be used—to the extent possible—in combination with and/or in the context of other particular aspects and embodiments of the invention, and in the invention generally.

While multiple embodiments are disclosed, still other embodiments of the present invention will become apparent to those skilled in the art from this detailed description. The invention is capable of myriad modifications in various obvious aspects, all without departing from the spirit and scope of the present invention. Accordingly, the drawings and descriptions are to be regarded as illustrative in nature and not restrictive.

In accordance with embodiments of the present invention, a menstrual cup case may comprise of three segments: a first/top segment referred to as the superior segment, a second/central segment referred to as the median segment, and the third/lower segment referred to as the inferior segment. In alternate embodiments, the median segment is absent and the superior segment is directly connected to the inferior segment. Each of the superior and inferior segments have their own unique purpose. In the preferred embodiments, the inferior segment is the cleaning cavity whereas the superior segment is the drying and storage cavity. However, in alternative embodiments, the superior and inferior segment may be switched such that the cleaning function is accomplished in the superior segment and the drying function is accomplished in the inferior segment. In select embodiments a removable structure, such as a gasket, is configured within the median cavity which sequesters the water and/or cleaning agents in one cavity while allowing the other cavity to remain dry. In alternate embodiments, the median segment is configured with a more permanent structure such a wall. Accordingly, in select embodiments the median segment shares functionality with the superior segment and the inferior segment. Irrespective of the number of segments, each segment of the menstrual cup case is severable and can be attached in any order per the user's preference.

In accordance with embodiments of the present invention, the menstrual cup case provides for the ability to sanitize the menstrual cup with readily available resources such as water. However, water by itself is not sufficient to fully remove protein, lipids, and other residue from menstrual blood. Accordingly, it is a feature of the invention to receive an inert cleaning agent within the menstrual case. When cleaning is needed, water or other reactive reagent can be used to activate the cleaning agent.

Alternate methodology of cleaning are also envisioned. As an illustration, instead of water, cleaning can be accomplished using hydrogen peroxide. Hydrogen peroxide is a known sterilant that kills infection-causing organisms such as *E. coli, Candida*, and *Gardnerella vaginalis* on surfaces. Yet, despite the cleaning ability of hydrogen peroxide, this substance can be an irritant and harmful. Accordingly, in certain embodiments the inferior segment is configured with a platinum disk that neutralizes the hydrogen peroxide. The platinum disk is designed for multiple uses, minimizing the need to carry extra components for proper cleansing.

Thus it is a feature of this invention to provide for compartmentalized sections that allow for the cleaning, drying, and storage of the menstrual cup. It is also a feature of the invention to be lightweight, compact, leak-proof, and sturdy. A further description of the invention illustrates how the aforementioned features are accomplished.

In accordance with embodiments of the present invention, the menstrual cup case is compact, leak-proof, and sturdy. In certain embodiments, the menstrual cup case is a substantially hollow case. While preferably cylindrical, other shapes are also envisioned. The cylindrical shape allows the menstrual case to be compact while the shape disperses stress rendering it a structurally sound formation. The menstrual case is segmented into at least two, but preferably three segments. The median segment serves as a linking piece between the superior and inferior segments so that the cleaning reagents do not leak into the drying and storage compartment.

According to certain embodiments, a segment may be reversibly attached to another segment. In some embodiments, each segment is comprised of an attachment means such as threads that enable screwing of one compartment to another compartment. According to alternate embodiments, the segments may be irreversibly connected but there is a door along a longitudinal portion of the menstrual cup case. The door is also configured with a gasket or another leak-proof material generally along the perimeter of the door. The door is also configured with a gasket along a cross-section to seal in liquid in the relevant compartment.

Turning towards the drawings, FIG. 1 illustrates the preferred embodiment of the current invention (100) in cylindrical configuration. In the preferred embodiment, the invention (100) comprises a superior segment (101), a median segment (102), and an inferior segment (103). The superior segment (101) is where the menstrual cup is positioned after cleaning for air-drying and storage. It generally comprises a top surface (105) that extends downwards as sidewalls (106) around a hollow area. In certain embodiments, the top surface comprises of one or more airholes or slits to promote evaporation. In the preferred embodiment, the top surface displays a slight dome configuration. Also in a preferred embodiment, the central area of a top surface (105) of the superior segment comprises of a hollowed protrusion (107), or a loop, for securing attachment means such as a string, chain, or carabiner. In the preferred embodiment, the sidewall (106) is configured with a non-slip means (110). In some embodiments, the non-slip means is grooves etched into the sidewall that extend towards the bottom end of the superior segment. In select embodiments, the bottom end of the superior segment is configured with a lip (108). The relative size of the superior segment (as compared to the other segments) can vary depending on the type of menstrual cup. If the menstrual cup is collapsible, a relatively smaller superior segment is necessary. Alternatively, if the menstrual cup is non-collapsible, a relatively larger superior segment is necessary.

Next is the median segment (102) which in preferred embodiments, connects the superior segment to the inferior segment. In the preferred embodiment, the median segment is generally cylindrical and hollow. At an external surface, the median segment is configured with a lip at a top (109a) and bottom surface (109b). In the preferred embodiment, the median segment does not comprise of a non-slip means. However, alternate embodiments envision non-slip means on the exterior surface of the median segment, including but not limited to grooves (see FIG. 8).

Finally, the menstrual cup case (100) comprises of an inferior segment (103). In preferred embodiments, the top of the inferior segment comprises of a lip (111) that extends downwards to form a generally cylindrical wall towards a bottom surface (not shown).

Figure 2:
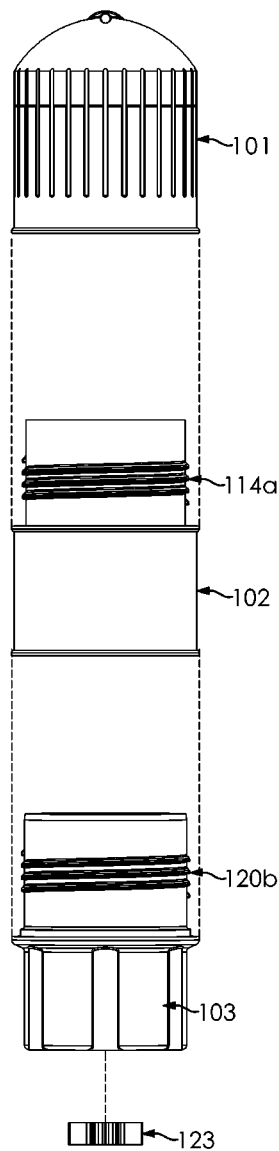
FIG. 2 illustrates an exploded, front-facing view of the preferred embodiment of the current invention.

FIG. 2 is an exploded view of the preferred embodiment of the menstrual cup case. As illustrated, the median segment is designed to integrate with the superior segment and the inferior segment. In select embodiment, the median segment is configured with at least two attachment means. In the illustrated embodiment, attachment means (114a) located on a top division of the median segment connects with a corresponding attachment means (not shown) located within the superior segment. Meanwhile, the attachment means (not shown) located on a bottom division of the median segment connects with a corresponding attachments means (120b) located on the inferior segment. Also visible in FIG. 2 is a cleaner holder (123) configured to hold the cleaner reagents.

Figure 3:
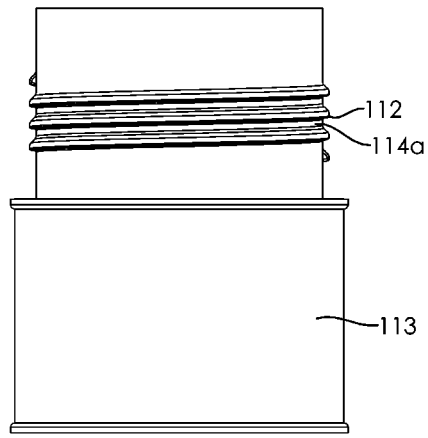
FIG. 3 illustrates a front facing view of the preferred embodiment of the median segment of the current invention.

FIG. 3 is an isolated illustration of the median segment (102) that shows components not readily visible when the menstrual cup case (100) is fully assembled. In the preferred embodiment, the median segment comprises of a top division (112) and a bottom division (113). The top division extends from the bottom division and is not separable. However, in alternate embodiments, the top division and bottom division may be reversibly connected. Each division comprises of an attachment means to connect with another segment.

The top division is typically narrower in diameter than the bottom division. The top division is configured with an attachment means (114a) that couples to a corresponding attachment means on the superior segment (not shown). According to preferred embodiments, the top division comprises of an attachment means on the exterior surface so that it can couple, connect or integrate to the corresponding attachment means located at a bottom portion of the superior segment (not shown). Likewise, the bottom portion of the superior segment is wider than the top division so that the top division can be inserted into the superior segment. According to the illustrated embodiment, the exterior surface of the top division is configured with an attachment means in the form of a helical ridge that can screw into the corresponding receiving helical ridges within the superior segment. However, alternate embodiments include other attachment means.

Likewise, the bottom division of the median segment is configured with an attachment means (not shown) towards the bottom, interior surface. In the illustrated embodiment, the bottom division is configured to fit over the inferior segment. As such, the bottom division includes an attachment means, such as a helical ridge, within the interior surface. However, alternative embodiments are also envisioned.

According to alternative embodiments, the median segment does not have a top division and a bottom division. In one embodiment, the median segment comprises of attachments means on its interior surface, preferably helical ridges. In such embodiment, the median segment is received over both the superior and inferior segments, that each have their corresponding attachment means on an outside surface. In other alternate embodiments, the median segment comprises of a narrower "top" division at each top and bottom end, where each top division includes an attachment means at an external surface. In such embodiment, the median segment functions as a "male" piece that is received within the superior segment and the inferior segment.

According to as yet further alternative embodiments, any type of attachment means may be used to connect the segments. For example, each segment may be connected to another segment by mechanical fasteners such as latches. In embodiments configured with latches, one way to connect the segments is to fasten the latches at an external surface. For example, at least one latch comprising of a rod is affixed to the external surface of the median segment while the receiving component is affixed on the external surfaces of the other segments. To latch the product, the rod slides into the receiving component.

FIG. 4 illustrates the preferential use of a gasket (115) that is situated within the median segment. FIG. 4a illustrates a gasket from a top perspective whereas FIG. 4b shows an underside view of the gasket within the median segment while FIG. 4c and FIG. 4d show isolated top and underside views. The gasket functions to provide a waterproof seal so that the cleaning area is physically separated from the drying/storage area. In the preferred embodiment, the gasket is generally planar with a bulge (116) protruding from the central area on a top surface. The bulge generally functions to prevent and/or release a menstrual cup from vacuum. The bottom surface of the gasket is configured with one or more cup-stand hooks (117). In the preferred embodiment, the cup-stand hooks are equally spaced around the perimeter of the gasket. The cup-stand hooks are configured so they may secure a menstrual cup case around the cup's wide base area. In general, the cup-stand hooks are projections within which a flexible menstrual cup is fitted through and held in place. In select embodiments, the menstrual cup may be grappled by the hooks. In an alternate embodiment, the cup-stand hooks are U-shaped, so a menstrual cup can latch onto the hook.

FIG. 5 illustrates a preferred embodiment of the inferior segment. The inferior segment is generally hollow comprising of a sidewalls and a bottom, planar surface. The preferred embodiment of the inferior segment includes a top division (118) and a bottom division (119). In the preferred embodiment, the top division of the inferior segment is configured with an attachment means (120a). In the illustrated example, the attachment means are helical ridges that are received within the corresponding attachment means (not shown) located within the bottom division of the median segment and twisted in to seal the cup. However, alternative attachment means are also envisioned. An O-ring (122) is configured around the external circumference to prevent leakage of any liquid from within the case. According to preferred embodiments, the bottom division includes gripping grooves (121) that provide for a sturdier grip.

According to embodiments, the inferior segment is configured with a cleaner holder (123). The cleaner holder is configured to receive a cleaning agent such as liquid or powder soap. Accordingly, in select embodiments, the cleaner holder may be a hollow cavity.

Figure 6:
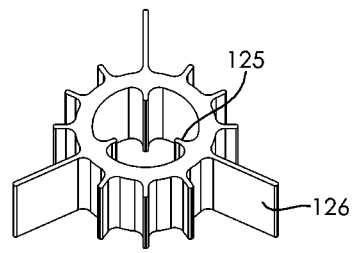
FIG. 6 illustrates a perspective view of a cleaning holder according to the preferred embodiment of the current invention.

However, according to preferred embodiments, the cleaner holder is a disk receiver (123). As illustrated in FIG. 6, the disk receiver is a circular ring. While hollow within, the interior wall of the disk receiver is configured with at least one, but multiple projections (125) that are oriented towards the center of the disk. Similarly, the outside disk is configured with projections (126) that project away from the center of the disk. In the illustrated embodiment, the outside projections are of two different sizes. The disk receiver is configured to receive platinum disks which comprise of hydrogen peroxide. The platinum disk is a neutralizer that contains hydrogen peroxide. The disk catalyzes the decomposition of the hydrogen peroxide to water over time.

According to select embodiments, the inferior segment also comprises of a peg (124) that is erected from the bottom surface. The peg is used to allow a menstrual cup to stand upright within the case. To use the peg, the stem end of a menstrual cup is positioned through the peg (if there is a hole at the stem end) or the stem end is positioned on top of the top surface of the peg. In order to provide further support to the menstrual cup so that it remains standing, according to embodiments of the current invention, the inferior segment further includes a least one cup stand guide (125). The cup stand guides are walls that are erected from the bottom surface and sidewall of the inferior segment. In embodiments, the cup stand guides are configured to provide side support to the menstrual cup by minimizing areas where it can move. According to preferred embodiments, the cup stand is configured into a "U" shape to hold the cup upright.

Figure 7:
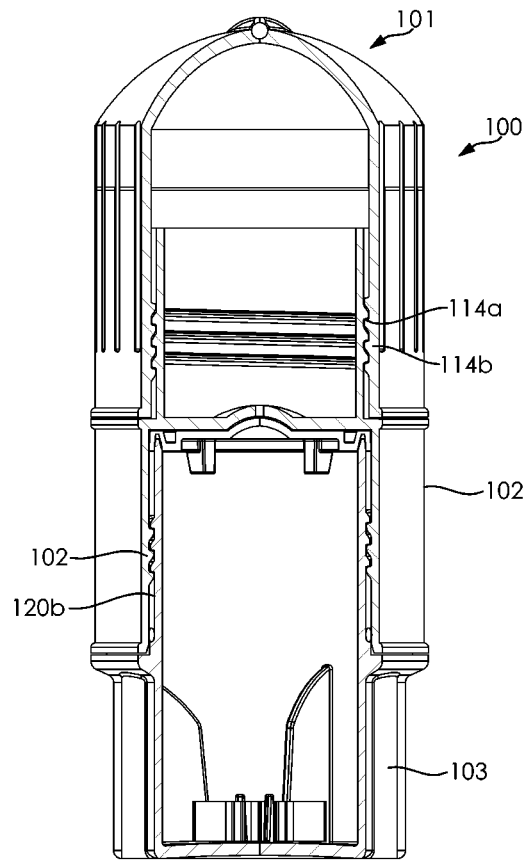
FIG. 7 illustrates a cross-sectional view of a preferred embodiment of the current invention.

FIG. 7 illustrates a cross-section view of the current invention (100). Visible in this view is the superior segment (101), the median segment (102) and the inferior segment (103). Also visible is the preferred embodiment of the segments connect. The median segment links both the superior segment and the inferior segment. The median segment is comprised of both a top division and a bottom division. Each division is configured with an attachment means. In the preferred embodiment, the top division includes the attachment means (114a) on its exterior surface whereas the bottom division includes the attachment means 120(a) on its interior surface. In greater detail, the attachment means (114a) of the top division connects, preferably screws into, the corresponding attachment means (114b) this is fashioned within the interior of the superior segment. Likewise, the attachment means (120a) of the bottom division connects, preferably screws into, the corresponding attachment means (120b) of the inferior segment.

According to the preferred embodiment, the menstrual cup case is configured so that the cup faces upward (the stem is on the bottom and the collection cavity is on the top, facing the superior segment). This orientation of the menstrual cup is best suited to prevent air from collecting in the cup. Furthermore, this orientation prevents any cleaning solution from reaching the inside of the menstrual cup, causing it to remain contaminated.

FIG. 8 illustrates alternative embodiments of the current invention. FIG. 8a and FIG. 8b both display embodiments where the median segment is configured with griping groves (127) along an exterior surface. As illustrated in FIG. 8 and described below, the structural features of the current invention may be transposed, added, or deleted.

As a first example, the clean cavity of the current invention may be in the superior segment while the inferior segment stores the menstrual cup. In such embodiment, the cleaning holder is situated underneath the top surface of the superior segment.

According to some embodiments of the current invention, at least one segment comprises of finger grips to prevent accidental slippage of the menstrual cup case. According to the preferred embodiments, each segment of the menstrual cup comprises of finger grips (121).

According to alternate embodiments of the current invention, each segment of the menstrual cup case may also serve as a storage unit. As an illustration, according to one alternate embodiment, the median segment may serve as a storage unit to hold the sterilizing tablets while the menstrual cup is stored in another segment.

According to select embodiments of the current invention, a ventilation system is included to avoid building excessing pressure within the menstrual case. According to preferred embodiments, the mechanism to relieve this pressure provides for air flow in one direction to prevent the intrusion of organic and non-organic contaminants. Accordingly, the preferred ventilation system includes an elastomeric membrane comprising of a slit or one or more holes through which excess pressure can be vented in a controlled manner. Further embodiments include a seal affixed to the menstrual cup case (preferably by using O-rings or gaskets) in order to contain fluids within the system and exclude contaminants while still allowing for ventilation. Other ventilation mechanisms adapted by persons skilled in the arts is also envisioned.

According to certain embodiments, the current invention is leak proof. According to select embodiments, each segment is configured with a lip so that when two segments are connected, the two lips create a seal to prevent leakage of contents within the membrane. The seal created by the lips may, in select embodiments, be reinforced with static O-ring seals and/or gaskets. According to preferred embodiments, the ingress protection standard for the current invention permits for the case to be leakproof (so that liquid does not enter or egress the menstrual cup case) despite being submerged for thirty (30) minutes at one (1) meter of depth.

According to an embodiment of the current invention, the menstrual cup case is sized to hold approximately 100 mL (~3.4 fl. oz.) of liquid. According to embodiments, the menstrual cup case is capable of storing approximately 7, aspirin-sized tablets. Alternate embodiments include menstrual cup cases that are capable of holding more or less volume.

According to embodiments of the current invention, the menstrual cup case is comprised of materials capable of withstanding robust or austere environmental conditions but is also lightweight for portability. Further, the material is non-reactive so it does not interfere with cleaning of the menstrual cup. Example of suitable material include plastic, rubber, silicone, ceramic, and stainless steel. Various embodiments may include a combination of one or more of the aforementioned materials.

To cleanse using the menstrual cup case, a cleaning agent may be added. As a first illustration, the cleaning agent may be an ordinary cleaning tablet that is added to the menstrual cup. In this method, a menstrual cup is inserted into the menstrual cup case and water is added. A cleaning tablet, such as, but not limited to an all-natural, biodegradable chlorine tablet is added, and the menstrual cup case is sealed. Subsequently, the user can allow the case to rest as the cleaning agent functions to cleanse or, if desired, shake the case for additional agitation.

As a second illustration, the cleaning agent may be ozonated water. Ozonated water is a triatomic molecule that contains three oxygen atoms. It has also been reported to possess antibacterial and sterilant properties. It has been shown that after exposure to ozonated water for thirty (30) seconds, 99.99% of infection-causing microorganisms are eliminated. In certain embodiments, the user places the menstrual cup in a segment of the menstrual cup case and adds an effective amount of water, preferably at room temperature. After approximately thirty (30) seconds, the water may be discarded. However, since ozonated water is unstable and has a short half-life, it decomposes into molecular oxygen ($O_2$). Thus, there is little, if any, downside in keeping the menstrual cup exposed to the ozonated water for a protracted period of time.

According to certain embodiments of the current invention, the menstrual cup case devise comprises of an ozone generator capable of converting water into ozonated water. According to one embodiment, the menstrual cup case is comprised of an electrolytic cell. The electrolytic cell includes one free-sanding diamond electrode and a second electrode or a free-standing diamond separated by a membrane as described in U.S. Pat. No. 8,980,079, incorporated herein by reference. In alternate embodiments, the ozone generator is comprised of fluororesin type cation exchange membrane centrally located between an anode and a cathode, as described in U.S. Pat. No. 8,815,064. Irrespective of the type of ozone generator, the menstrual cup case is further comprised of a power source, for example batteries, that operates the ozone generator. In certain embodiments, the ozone generator is configured within its own segment. The segment also comprises of tubes that are able to deliver the ozonated water from the ozone generator segment to the cleansing segment. In select embodiments, cleansing segment may be configured with a spray nozzle so the ozonated water is sprayed onto the menstrual cup for cleaning.

Alternatively, the case may be configured with a cleaning agent or a reagent. As an illustration, the menstrual cup case may be configured with a neutralizing disk held in place by removable peg (rather than used a support for a menstrual cup in other embodiments). In this embodiment, the neutralizing disk is comprised of a platinum compound. In some embodiments, the neutralizing disk is star-shaped. In particular, the disc comprises of multiple grooves surrounding the disc. Accordingly, the case is configured with extending flaps to situate and firmly hold the neutralizing disk. In further embodiments, the case further comprises of a peg designed to fit within the center of the neutralizing disk to add reinforcement to firmly secure the neutralizing disk. The peg may be flexible or it may be stiff. To cleanse a menstrual cup, a tablet comprising of hydrogen peroxide is added to the menstrual cup case along with a liquid solvent such as water. The hydrogen peroxide reacts with the platinum in the neutralizing disk and activates cleaning of the menstrual cup.

In embodiments, the cleaning agent is "inactive" or "inert". In the preferred embodiment, the cleaning agent is the form of a dry powder packed in a disk and held in place with a removable peg. Such cleaning agent has a long shelf-life and can be activated multiple times before replacement is required. In the preferred embodiment, the menstrual cup is inserted in the inferior segment. A reactive agent such as water is added to the inferior segment and the segment is sealed by attaching (at least) the median segment. The reaction of the cleaning agent and the reactive agent cleanses the menstrual cup. Once the menstrual cup is cleaned, it is removed from the inferior segment and placed in the superior segment where it is allowed to dry and remained stored until use is required. Alternatively, the menstrual cup may remain stored in the inferior segment.

According to an embodiment of the current invention, a method of cleaning a menstrual cup is described.

It should be noted that the features illustrated in the drawings are not necessarily drawn to scale, and features of one embodiment may be employed with other embodiments as the skilled artisan would recognize, even if not explicitly stated herein. Descriptions of well-known components and processing techniques may be omitted so as to not unnecessarily obscure the embodiments.

In the present disclosure, various features may be described as being optional, for example, through the use of the verb "may;", or, through the use of any of the phrases: "in some embodiments," "in some implementations," "in some designs," "in various embodiments," "in various implementations,", "in various designs," "in an illustrative example," or "for example;" or, through the use of parentheses. For the sake of brevity and legibility, the present disclosure does not explicitly recite each and every permutation that may be obtained by choosing from the set of optional features. However, the present disclosure is to be interpreted as explicitly disclosing all such permutations. For example, a system described as having three optional features may be embodied in seven different ways, namely with just one of the three possible features, with any two of the three possible features or with all three of the three possible features.

In the present disclosure, the term "any" may be understood as designating any number of the respective elements, i.e. as designating one, at least one, at least two, each or all of the respective elements. Similarly, the term "any" may be understood as designating any collection(s) of the respective elements, i.e. as designating one or more collections of the respective elements, a collection comprising one, at least one, at least two, each or all of the respective elements. The respective collections need not comprise the same number of elements.

While various embodiments of the present invention have been disclosed and described in detail herein, it will be apparent to those skilled in the art that various changes may be made to the configuration, operation and form of the invention without departing from the spirit and scope thereof. In particular, it is noted that the respective features of embodiments of the invention, even those disclosed solely in combination with other features of embodiments of the invention, may be combined in any configuration excepting those readily apparent to the person skilled in the art as nonsensical. Likewise, use of the singular and plural is solely for the sake of illustration and is not to be interpreted as limiting.

In the present disclosure, all embodiments where "comprising" is used may have as alternatives "consisting essentially of," or "consisting of." In the present disclosure, any method or apparatus embodiment may be devoid of one or more process steps or components. In the present disclosure, embodiments employing negative limitations are expressly disclosed and considered a part of this disclosure.

Certain terminology and derivations thereof may be used in the present disclosure for convenience in reference only and will not be limiting. For example, words such as "upward," "downward," "left," and "right" would refer to directions in the drawings to which reference is made unless otherwise stated. Similarly, words such as "inward" and "outward" would refer to directions toward and away from, respectively, the geometric center of a device or area and designated parts thereof. References in the singular tense include the plural, and vice versa, unless otherwise noted.

The term "comprises" and grammatical equivalents thereof are used herein to mean that other components, ingredients, steps, among others, are optionally present. For example, an article "comprising" (or "which comprises") components A, B and C can consist of (i.e., contain only) components A, B and C, or can contain not only components A, B, and C but also contain one or more other components.

Where reference is made herein to a method comprising two or more defined steps, the defined steps can be carried out in any order or simultaneously (except where the context excludes that possibility), and the method can include one or more other steps which are carried out before any of the defined steps, between two of the defined steps, or after all the defined steps (except where the context excludes that possibility).

The term "at least" followed by a number is used herein to denote the start of a range beginning with that number (which may be a range having an upper limit or no upper limit, depending on the variable being defined). For example, "at least 1" means 1 or more than 1. The term "at most" followed by a number (which may be a range having 1 or 0 as its lower limit, or a range having no lower limit, depending upon the variable being defined). For example, "at most 4" means 4 or less than 4, and "at most 40%" means 40% or less than 40%. When, in this specification, a range is given as "(a first number) to (a second number)" or "(a first number)-(a second number)," this means a range whose limit is the second number. For example, 25 to 100 mm means a range whose lower limit is 25 mm and upper limit is 100 mm.

Many suitable methods and corresponding materials to make each of the individual parts of embodiment apparatus are known in the art. According to an embodiment of the present invention, one or more of the parts may be formed by machining, 3D printing (also known as "additive" manufacturing), CNC machined parts (also known as "subtractive" manufacturing), and injection molding, as will be apparent to a person of ordinary skill in the art. Metals, wood, thermoplastic and thermosetting polymers, resins and elastomers as described herein-above may be used. Many suitable materials are known and available and can be selected and mixed depending on desired strength and flexibility, preferred manufacturing method and particular use, as will be apparent to a person of ordinary skill in the art.

Any element in a claim herein that does not explicitly state "means for" performing a specified function, or "step for" performing a specific function, is not to be interpreted as a "means" or "step" clause as specified in 35 U.S.C. § 112 (f). Specifically, any use of "step of" in the claims herein is not intended to invoke the provisions of 35 U.S.C. § 112 (f).

A number of implementations have been described. Nevertheless, it will be understood that various modifications may be made. For example, advantageous results may be achieved if the steps of the disclosed techniques were performed in a different sequence, or if components of the disclosed systems were combined in a different manner, or if the components were supplemented with other components. Accordingly, other implementations are contemplated within the scope of the following claims.

The invention claimed is:

1. A menstrual cup case comprising:
a generally hollow superior segment with a top surface;
a generally hollow median segment; and
a generally hollow inferior segment with a bottom surface,
wherein the median segment along a top surface further comprises a gasket.

2. The menstrual cup case of claim 1, wherein the median segment further comprises a top division configured to receive the superior segment and a bottom division configured to receive the inferior segment.

3. The menstrual cup case of claim 2 wherein the top division has a smaller circumference than the superior segment.

4. The menstrual cup case of claim 3, wherein the median segment further comprises a first attachment means on an exterior surface.

5. The menstrual cup case of claim 4, wherein the first attachment means integrates with a corresponding attachment means within the superior segment.

6. The menstrual cup case of claim 3, wherein the bottom division comprises a second attachment means on an interior surface.

7. The gasket of claim 1, wherein a central region of said gasket comprises of a bulge.

8. The menstrual cup case of claim 1, wherein the gasket further comprises one or more cup-stand hooks.

9. The menstrual cup case of claim 8, wherein a plurality of cup-stand hooks of said one or more cup-stand hooks are arranged equidistant around a perimeter of said gasket.

10. The menstrual cup case of claim 1, wherein said inferior segment further comprises a cleaner holder.

11. The menstrual cup case of claim 10, wherein said cleaner holder comprises of a ring.

12. The menstrual cup case of claim 11, wherein said ring further comprises of one or more walls extending from an outer surface of said ring.

13. The menstrual cup case of claim 11, wherein said ring further comprises at least two sets of walls that extend from an outer surface of said ring and wherein one set of walls of said at least two sets of walls is smaller in width than at least one other set of walls of said at least two sets of walls.

14. The menstrual cup case of claim 11, further comprising a peg provided within a hollow center of said ring.

15. The menstrual cup case of claim 14, wherein said peg is comprised of flexible material.

16. A menstrual cup case comprising a generally hollow storage segment, a generally hollow cleaning segment, and a gasket provided between said storage segment and said cleaning segment, said gasket configured to fluidly seal said menstrual cup case between said storage segment and said cleaning segment.

17. The menstrual cup case of claim 16, wherein said gasket further comprises a bulge at a center of said gasket.

18. The menstrual cup case of claim 16, wherein said gasket further comprises at least once cup-stand hook.

19. The menstrual cup case of claim 16, wherein said cleaning segment further comprises a cleaner holder.

20. A menstrual cup case comprising:
a generally hollow superior segment;
a generally hollow median segment comprising a top division and a bottom division;
a generally hollow inferior segment; and
a gasket,
wherein said top division further comprises a first attachment means on an exterior surface of said top division that fastens to a corresponding second attachment means provided as part of said superior segment;
wherein said bottom division further comprises a third attachment means on an interior surface of said bottom division that fastens to a corresponding fourth attachment means provided as part of said inferior segment, and
wherein a bottom surface of said gasket further comprises at least one cup stand hook.

* * * * *